US006436140B1

(12) United States Patent
Liu et al.

(10) Patent No.: US 6,436,140 B1
(45) Date of Patent: Aug. 20, 2002

(54) EXPANDABLE INTERBODY FUSION CAGE AND METHOD FOR INSERTION

(75) Inventors: Mingyan Liu, Bourg-la-Reine; Loic Josse, Montargis, both of (FR)

(73) Assignee: Sofamor S.N.C., Roissy CDG Cedex (FR)

( * ) Notice: Subject to any disclaimer, the term of this patent is extended or adjusted under 35 U.S.C. 154(b) by 0 days.

(21) Appl. No.: 09/763,073

(22) PCT Filed: Aug. 26, 1999

(86) PCT No.: PCT/IB99/01478

§ 371 (c)(1),
(2), (4) Date: May 16, 2001

(87) PCT Pub. No.: WO00/12033

PCT Pub. Date: Mar. 9, 2000

(30) Foreign Application Priority Data

Aug. 28, 1998 (FR) ............................................ 98 10832

(51) Int. Cl.[7] .................................................. A61F 2/44
(52) U.S. Cl. .................................. 623/17.11; 623/17.15
(58) Field of Search ........................... 623/17.11, 17.15, 623/16.11

(56) References Cited

U.S. PATENT DOCUMENTS

| 4,714,469 A | 12/1987 | Kenna |
| 4,863,476 A | 9/1989 | Shepperd |
| 5,059,193 A | 10/1991 | Kuslich |
| 5,171,278 A | 12/1992 | Pisharodi |
| 5,236,460 A | 8/1993 | Barber |
| 5,390,683 A | 2/1995 | Pisharodi |
| 5,522,899 A | 6/1996 | Michelson |
| 5,554,191 A | 9/1996 | Lahille et al. |
| 5,609,635 A | 3/1997 | Michelson |
| 5,653,763 A | 8/1997 | Errico et al. |
| 5,658,335 A | 8/1997 | Allen |

(List continued on next page.)

FOREIGN PATENT DOCUMENTS

| DE | 44 16 605 C1 | 5/1994 |
| EP | 0 425 542 B1 | 3/1995 |
| FR | 2 753 368 A1 | 3/1998 |
| WO | WO-92/14423 A1 * | 9/1992 |
| WO | WO 97/00054 A1 | 1/1997 |
| WO | WO 98/48738 A1 | 11/1998 |
| WO | WO 99/42062 A1 | 8/1999 |

Primary Examiner—Jeffrey A. Smith
(74) Attorney, Agent, or Firm—Woodard, Emhardt, Naughton, Moriarty & McNett (57) ABSTRACT

An expandable interbody fusion device in one embodiment includes a cylindrical body (10) defining a hollow interior (17) for receiving bone graft or bone substitute material. The body (10) is divided into a number of branches (24, 26, 40 and 41) connected to one another at a fixed end (20) and separated at an expandable end (18). The expandable cage may be inserted in its substantially cylindrical form and may be expanded by movement of an expansion member (50) to establish lordosis of the spine. The present invention provides an expansion member (50) that interacts with the interior surfaces of the device to maintain the cage in the expanded condition and provide a large internal chamber (17) for receiving bone in-growth material. Methods for insertion of the fusion device are also disclosed.

22 Claims, 9 Drawing Sheets

U.S. PATENT DOCUMENTS

| | | |
|---|---|---|
| 5,665,122 A | 9/1997 | Kambin |
| 5,683,394 A | 11/1997 | Rinner |
| 5,693,100 A | 12/1997 | Pisharodi |
| 5,702,391 A | 12/1997 | Lin |
| 5,702,455 A | 12/1997 | Saggar |
| 5,713,904 A | 2/1998 | Errico et al. |
| 5,723,013 A | 3/1998 | Jeanson et al. |
| 5,776,199 A | 7/1998 | Michelson |
| 5,782,832 A | 7/1998 | Larsen et al. |
| 5,865,848 A * | 2/1999 | Baker ..................... 623/17.15 |
| 5,928,284 A | 7/1999 | Mehdizadeh |
| 5,980,522 A | 11/1999 | Koros et al. |
| 6,045,579 A | 4/2000 | Hochshuler et al. |
| 6,048,342 A | 4/2000 | Zucherman et al. |
| 6,080,193 A | 6/2000 | Hochshuler et al. |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,129,763 A | 10/2000 | Chauvin et al. |
| 6,159,245 A | 12/2000 | Meriwether et al. |
| 6,176,882 B1 | 1/2001 | Biedermann et al. |
| 6,179,873 B1 | 1/2001 | Zientek |
| 6,193,757 B1 | 2/2001 | Foley et al. |
| 6,214,050 B1 | 4/2001 | Huene |
| 6,217,579 B1 | 4/2001 | Koros |

* cited by examiner

EXPANDABLE INTERBODY FUSION CAGE AND METHOD FOR INSERTION

The present Application claims foreign priority benefits of International Patent Application Number PCT/IB99/01478, filed Aug. 26, 1999, and French Patent Application Number FR98/10832, filed on Aug. 28, 1998, the contents of each application hereby being incorporated by reference.

BACKGROUND OF THE INVENTION

The present invention relates to an implantable device for promoting fusion between two adjacent bony structures and a method of inserting the same. More particularly, the invention relates to an expandable fusion cage that may be inserted, in a reduced size configuration, into an intervertebral space and expanded after insertion to provide a desired size. While the device according to the present invention may have application in other areas of the body, the present invention is preferably utilized for vertebral interbody fusion.

There have been an extensive number of attempts to develop an exceptional intradiscal implant that could be used to replace a damaged disc and yet maintain the stability of the disc interspace between adjacent vertebra, at least until complete arthrodesis is achieved. These "interbody fusion devices" have taken many forms. For example, one of the more prevalent designs takes the form of a cylindrical implant. These types of implants are presented by the patents to Bagby, U.S. Pat. No. 4,501,269; Brantigan, U.S. Pat. No. 4,878,915; Ray, U.S. Pat. Nos. 4,961,740 and 5,055,104; and Michelson, U.S. Pat. No. 5,015,247. In the cylindrical implants, the exterior portion of the cylinder can be threaded to facilitate insertion of the interbody fusion device, as represented by the Ray, Brantigan and Michelson patents. In the alternative, some of the fusion implants are designed to be pounded into the intradiscal space. This type of device is represented by the patent to Brantigan.

Interbody fusion devices can be generally divided into two basic categories, namely solid implants and implants that are designed to permit bone in-growth. Solid implants are represented by U.S. Pat. Nos. 4,879,915; 4,743,256; 4,349,921; and 4,714,469. The remaining patents discussed above include some aspect that allows bone to grow across the implant. It has been found that the devices that promote natural bone in-growth achieve a more rapid and stable arthrodesis. The device depicted in the Michelson patent is representative of this type of hollow implant which is typically filled with a bone growth inducing substance to promote bone growth into and through the device. This implant includes a plurality of circular apertures which communicate with the hollow interior of the implant, thereby providing a path for tissue growth between the vertebral end plates and the bone growth material within the implant. In preparing the intradiscal space, the end plates are preferably reduced to bleeding bone to facilitate the tissue in-growth. During fusion, the metal structure provided by the Michelson implant helps maintain the patency and stability of the motion segment to be fused. In addition, once arthrodesis occurs, the implant itself serves as a sort of anchor for the solid bony mass.

One problem that is not addressed by the above prior devices concerns maintaining and restoring the normal anatomy of the fused spinal segment. Naturally, once the disc is removed, the normal lordotic or kyphotic curvature of the spine is eliminated. With the prior devices, the need to restore this curvature is neglected. For example, adjacent vertebral bodies may be reamed with a cylindrical reamer that fits the particularly implant. In some cases, the normal curvature is established prior to reaming and then the implant inserted. However, this over-reaming of the posterior portion is generally not well accepted because of the removal of load bearing bone of the vertebrae and because it is typically difficult to ream through the posterior portion of the lower lumbar segment where the lordosis is the greatest. In most cases using implants of this type, no effort is made to restore the lordotic curvature so that the cylindrical implant is likely to cause a kyphotic deformity as the vertebrae settles around the implant. This phenomena can often lead to revision surgeries because the spine becomes imbalanced.

In each of the above-listed patents, the transverse cross-section of the implant is substantially constant throughout its length and is typically in the form of a right circular cylinder. Other implants have been developed for interbody fusion that do not have a constant cross-section. For instance, the patent to McKenna, U.S. Pat. No. 4,714,469 shows a hemispherical implant with elongated protruberances that project into the vertebral end plate. Further, U.S. Pat. No. 5,669,909 to Zdeblick et al., shows a truncated conical implant adapted to be threadedly received in the intervertebral space. However, these devices require an opening at least as large as the largest segment of the device. The requirement for such a relatively large opening may limit the use of such devices, particularly where access to the spine is limited due to obstructing vessels and neurological structures.

Still further implants have been developed that provide the ability to adjust the size of the implant after insertion. U.S. Pat. Nos. 5,665,122 to Kambin, 5,554,191 to LaHille et al., and 5,653,763 to Errico et at., disclose implants which provide at least some degree of adjustability of the height of the implant to restore lordosis. However; these implants do not allow the device to be easily and securely inserted into a disc space and the internal expansion mechanism limits the ability to pack the interior with a large amount of bone in-growth material.

FR 2,753,368 discloses an interbody implant formed by a cage having four longitudinal branches that can be simultaneously radially expanded by a wedge means. Consequently the cage is laterally expanded in an undesirable manner, harmful to the patient.

WO 97/00054 teaches an implant in two separated members, connected by a complicated means with end portion shaped for maintaining an angle between these members.

U.S. Pat. No. 5,683,394 discloses an implant formed by an integral cage with an end cap.

U.S. Pat. No. 5,702,455 relates to an implant formed by two tubular members having holes and connected by a threaded tube.

In view of the limitations of the prior devices, there remains a need for an interbody fusion cage capable of stabilizing the spine in a manner comparable to interbody implant designs presently in use, and at the same time providing a mechanism for restoring normal lordosis of the spine. After expansion, the implant should have an internal cavity adapted to receive bone graft or bone substitute to encourage bone growth through the expanded implant.

SUMMARY OF THE INVENTION

In response to the needs still left unresolved by the prior devices, the present invention contemplates an expandable fusion cage adapted to be inserted between a pair of vertebral bodies to restore the normal angular relation between adjacent vertebrae. In particular, a device according to the present invention comprises a body having an outer bone engaging surface and an inner surface defining an internal chamber and a retaining mechanism. The body has a fixed portion and an expandable portion. The expandable portion is divided into at least a first branch and a second branch, interconnected at the fixed portion. The first branch is moveable with respect to the second branch in the expandable portion to expand the overall size of the fusion cage. An expansion member is sized to be at least partially received within the internal chamber and has an outer surface adapted to engage the retaining mechanism. Movement of the expansion member within the internal chamber urges the first branch to move with respect to the second branch thereby expanding the expandable portion. The expansion member is retained in position by engagement with the retaining mechanism of the body.

In another aspect of the invention, an expandable intersomatic cage has a tubular body having an outer bone engaging surface and an inner surface defining an interior chamber. The inner surface further defines an inclined surface and a retaining mechanism. The body defines a fixed portion and a moveable portion, the inclined surface is disposed adjacent the moveable portion. In this aspect of the invention, an expansion member is included having an outer surface configured to engage the inclined surface and the retaining portion. Movement of the expansion member against the inclined surface moves the moveable portion to expand the cage. The expansion member is retained in position by engagement with the retaining mechanism.

In another embodiment, the invention contemplates an insertion tool cooperable with an expandable fusion implant. The insertion tool is operable to insert the implant and move the expansion member to expand the cage. A cage according to the present invention is utilized with an insertion tool having an outer sleeve adapted to engage the body of the cage to transmit compressive force to the cage. The insertion tool further includes an inner shaft moveably disposed within the outer sleeve. The inner shaft is sized to be inserted into at least a portion of the interior chamber of the cage. The inner shaft has a distal end configured to removably engage the expansion member, whereby movement of the inner shaft with respect to the outer sleeve moves the expansion member in relation to the cage.

In another aspect of the invention, methods are provided for insertion of an expandable intersomatic device. In one aspect a device according to the present invention is inserted into the disc space. The moveable portion of the device is positioned adjacent a portion of the vertebra requiring additional spacing. The expansion member is then moved within the internal chamber and against the moveable portion to expand the cage to the desired height. The expansion member may be engaged with the retaining mechanism to limit movement of the expansion member.

One object of the present invention is to provide an implant that has a reduced size insertion configuration and is expandable from the insertion configuration to a larger configuration.

Another object of the present invention is to provide an expandable implant that has a substantially unobstructed interior chamber to receive bone growth promoting material.

Still another object of the present invention is to provide a fusion cage configured for easy insertion and expandable to a larger size to establish lordosis.

Yet a further object of the present invention is to provide an improved method for inserting a fusion cage and restoring lordosis.

Related objects and advantages of the present invention will be apparent from the following description.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 1:
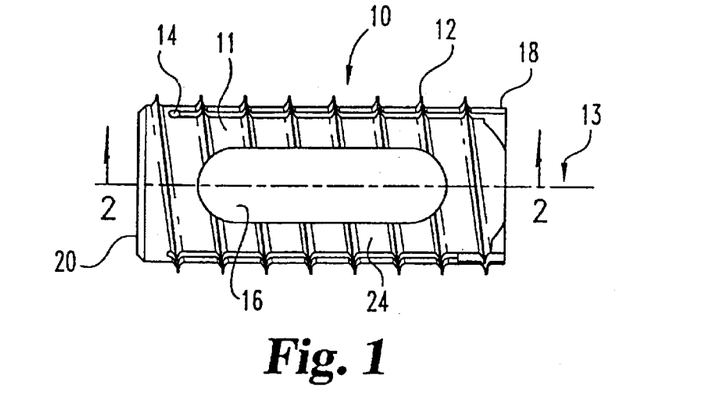
FIG. 1 is a top view of an expandable cage according to one embodiment of the present invention.
Figure 2A:
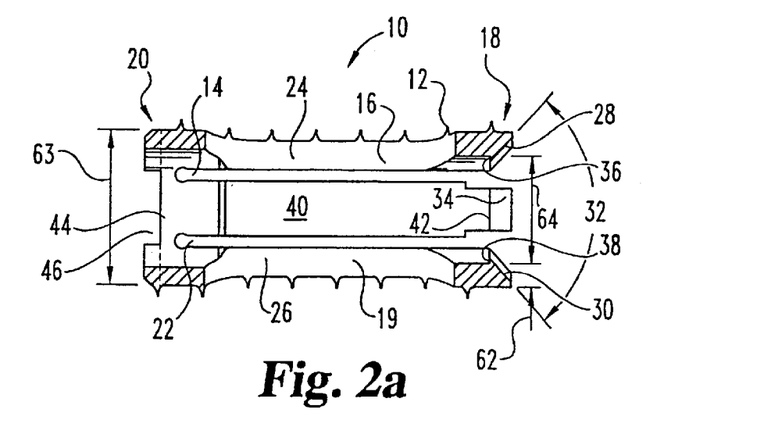
FIG. 2a is a side cross-sectional view of the device of FIG. 1.
Figure 2B:
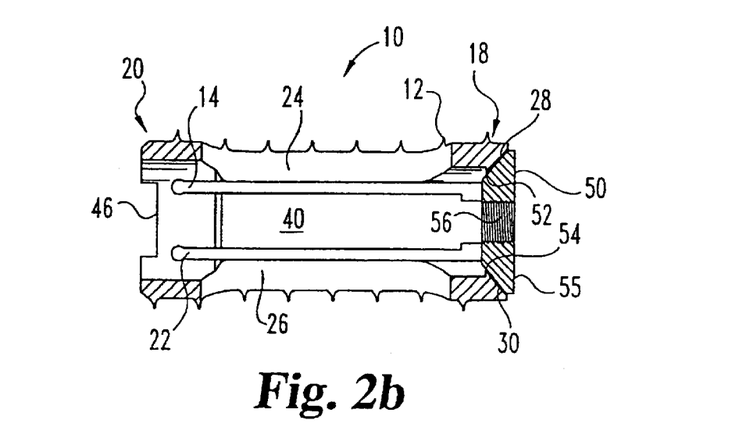
FIG. 2b is the device of FIG. 2a with the inclusion of an expansion wedge according to one embodiment of the present invention.
Figure 3:
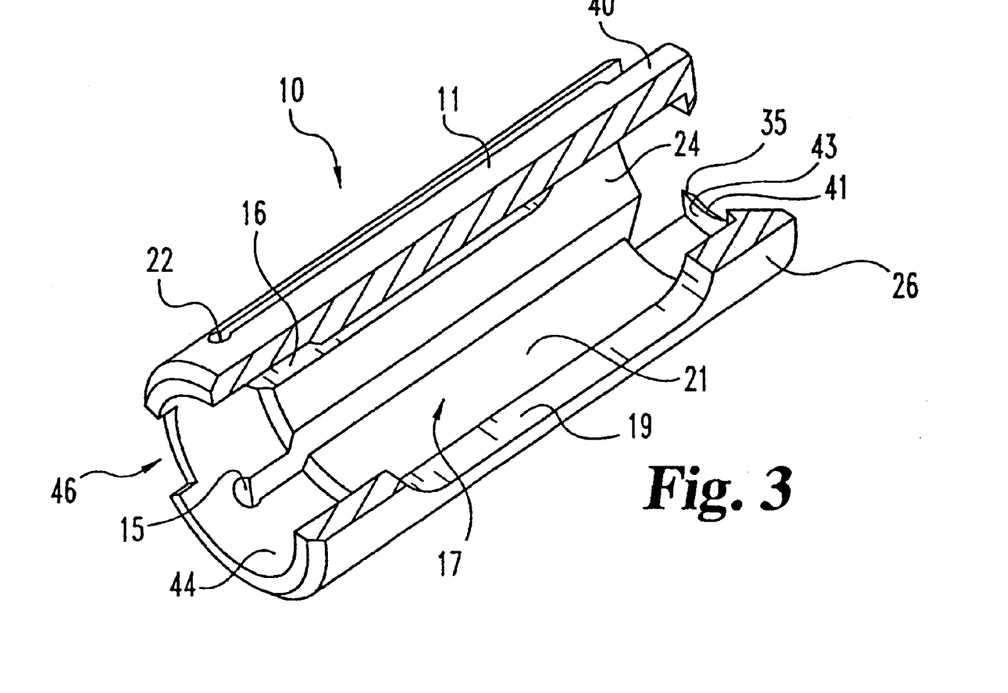
FIG. 3 is a partial cross-sectional perspective view of the expandable cage of FIG. 1 without an external thread pattern.

Referring now to FIGS. 1 through 3, there is shown a first embodiment of an expandable cage 10 in accordance with the present invention. In this embodiment of the invention, expandable cage 10 has a cylindrical outer surface 11 defining an external thread pattern 12 (not shown in FIG. 3)

adapted to engage two adjacent vertebra (see FIGS. 7a and 7b) and to advance the cage into the disk space as cage 10 is rotated about longitudinal axis 13. As shown most clearly in FIG. 3, expandable cage 10 is substantially hollow with inner surface 21 defining an internal cavity 17. Expandable cage 10 includes a bone in-growth window 16 formed through expandable branch 24 and an identical bone in-growth window 19 formed through expandable branch 26. These in-growth windows are adapted to permit communication between the vertebral bodies (FIG. 7) and internal chamber 17. In most application, bone growth promoting material will be placed within internal chamber 17 of expandable cage 10 to encourage bone to grow into and through fusion device 10.

As shown in the accompanying drawings, expandable cage 10 is preferably composed of four separate branches, each separated at expandable end 18 by a channel extending longitudinally from expandable end 18 toward fixed end 20. Referring now to FIG. 2a, first expandable branch 24 is separated from first fixed branch 40 by channel 14. In a similar manner, second expandable branch 26 is separated from first fixed branch 40 by channel 22. Each of channels 14 and 22 extends from expandable end 18 towards fixed end 20. The channels terminate in a slightly larger diameter radiused opening which preferably acts as a hinge during expansion of the device to concentrate stress and deformation adjacent fixed end 20. In a similar fashion, as shown in FIG. 3, second fixed branch 41 is separated from first expandable branch 24 by channel 15 and from second expandable branch 26 by a similar channel (not shown) Thus, expandable cage 10 is formed by four branches, each separated from the other at expandable end 18 by channels extending from outer surface 11 to internal chamber 17. The branches are connected at fixed end 20 by linking area 44 such that each of the branches may move substantially independent from each other at expandable end 18 while remaining connected to the device by linking area 44. Although the present embodiment utilizes integrally formed branches, it is contemplated that separate components may be joined to form the expandable cage without deviating from the invention.

While four separate branches are shown in a preferred embodiment, it is contemplated that more or less branches could be utilized without deviating from the spirit or scope of the invention. Moreover, although in a preferred embodiment the channels extend from outer surface 11 to internal chamber 17, it is contemplated that the channels may not extend to the interior chamber. Such a channel may be formed by an overlapping interface between two adjacent branches without creating an opening for bone in-growth into internal chamber 17. Further, although channels are shown as being preformed in the expandable cage, it is contemplated that the channels may be formed as the implanted is expanded. By way of example, and without limitation, this could occur by rupturing a frangible portion between adjacent branches or by deforming material disposed between adjacent branches.

In one aspect of the invention, internal chamber 17 comprises the majority of the volume of the entire cage 10. Specifically referring to FIG. 2a, external surface 11 defines a diameter 63, excluding threads 12. Internal chamber 17 has a diameter of at least 64, that is diameter 63 less twice the branch thickness 62.

In a preferred embodiment, branch thickness 62 is selected such that the volume of internal chamber 17, particularly with the inclusion of voids created by in-growth windows 16 and 19 and the various channels occupies the majority of the entire volume of cage 10. Thus, the present invention provides space for a large volume of bone growth promoting material to be inserted into the device to promote bone in-growth.

Adjacent expansion end 18, as shown in FIG. 2a with respect to branches 24, 40 and 26, each of the branches includes inclined surfaces 28, 34 and 30, respectively. Adjacent the internal termination of each of the inclined surfaces 28, 34 and 30, is formed an internal shoulder 36, 42 and 38, respectively. Referring to FIG. 3, branch 41 includes a similar inclined surface 35 and internal shoulder 43. As shown in FIG. 2a, arcuate inclined surfaces 28 and 30 are inclined at angle 32 with respect to each other. In a preferred embodiment, this angle is approximately 96°, although it is understood that a variety of angles could be utilized depending on the amount of expansion desired, and the distance an expansion member will need to travel to create the expansion.

Figure 4:
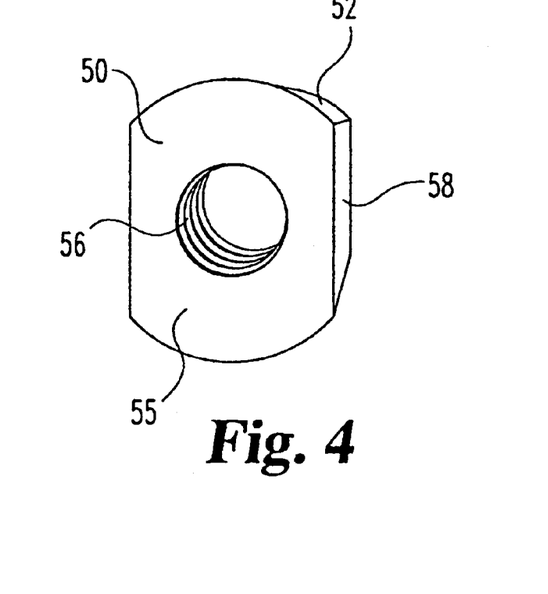
FIG. 4 is a perspective view of the expansion wedge of FIG. 2b.
Figure 5:
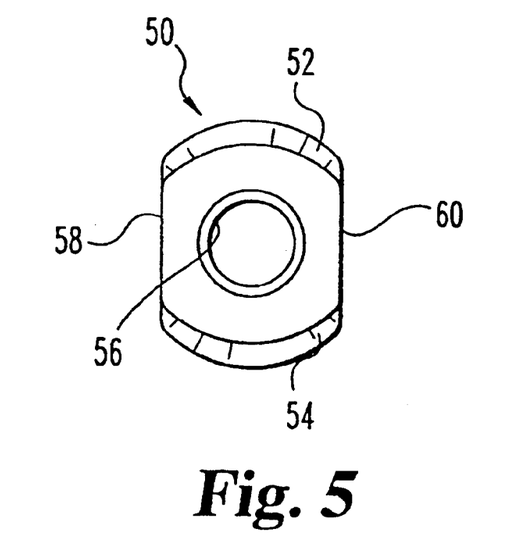
FIG. 5 is an end view of the expansion wedge of FIG. 4.

Referring now to FIG. 2b, cage 10 is shown with the inclusion of expansion wedge 50 disposed adjacent expandable end 18. Expansion wedge 50 is further illustrated in FIGS. 4 and 5. Expansion wedge 50 includes first and second opposed expansion wedge inclines 52 and 54, which have a tapering arcuate surface that mates with and corresponds to inclined surfaces 28 and 30 of branches 24 and 26, respectively. Wedge 50 includes side walls 58 and 60 with substantially planar surfaces adapted to engage inclined surfaces 34 and 35 of fixed branches 40 and 41, respectively. Further, expansion wedge 50 includes a central opening 56 which is adapted to receive a driving tool. In a preferred embodiment, central opening 56 is threaded to receive a correspondingly threaded end of a driving tool.

It will be understood that as wedge 50 is advanced toward fixed end 20, inclined surfaces 52 and 54 act upon inclined surfaces 28 and 30, respectively, to urge branches 24 and 26 apart from each other at expandable end 18. As expansion wedge 50 is inserted along inclined surfaces 28 and 30, branches 24 and 26 will tend to expand at expansion end 18 as deformation occurs adjacent fixed end 20. Substantially continuous linking material 44 links all of the branches and does not permit their expansion at fixed end 20. As wedge 50 is further advanced toward fixed end 20, the wedge is pushed beyond shoulders 36 and 38, such that wedge 50 is captured within cage 10. As a result of the engagement of back surface 55 of the wedge against shoulders 36 and 38, expansion wedge 50 is prevented from being expelled from the cage, and the cage is maintained in an expanded condition with the wedge securely held in position. It will be understood that the engagement of planar surfaces 58 and 60 on fixed branches 40 and 41, respectively, tends to deformably expand these branches little, if any, and therefore they remain substantially fixed in their original positions. Further, fixed branches 40 and 41 each include shoulders 42 and 43 which engage the back surface 55 of wedge 50 once it has passed beyond the shoulders. Thus, fixed branches 40 and 41 also tend to hold the wedge in place and prevent its expulsion from internal chamber 17.

Figure 8:
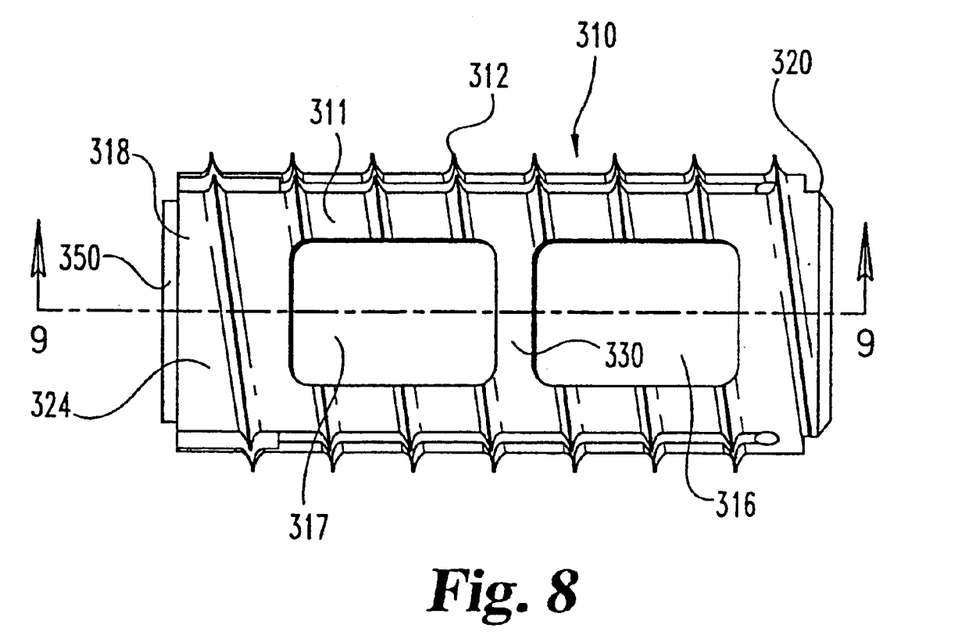
FIG. 8 is a top view of an alternative embodiment of the expandable cage of FIG. 1.
Figure 9:
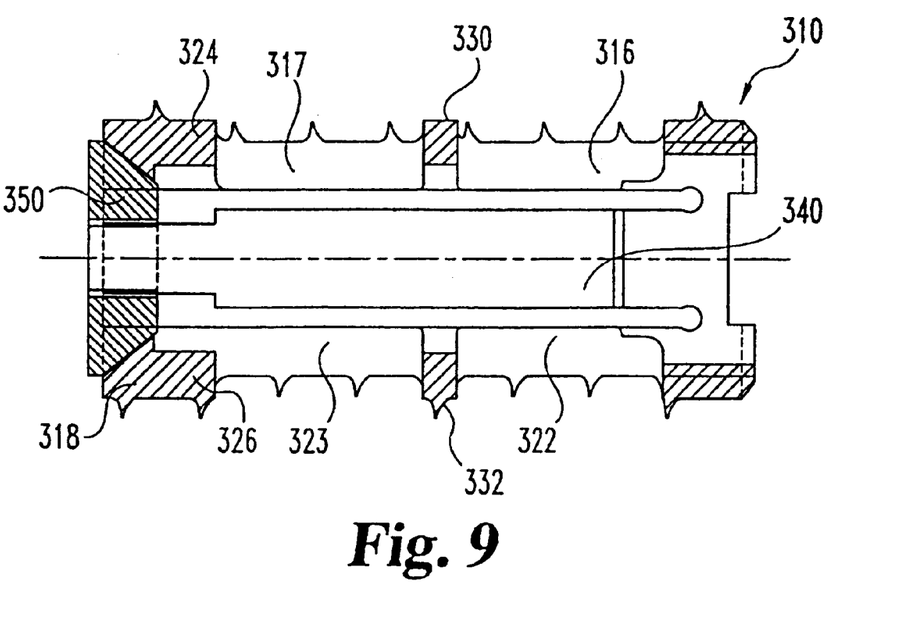
FIG. 9 is a side cross-sectional view of the expandable cage of FIG. 8.
Figure 10:
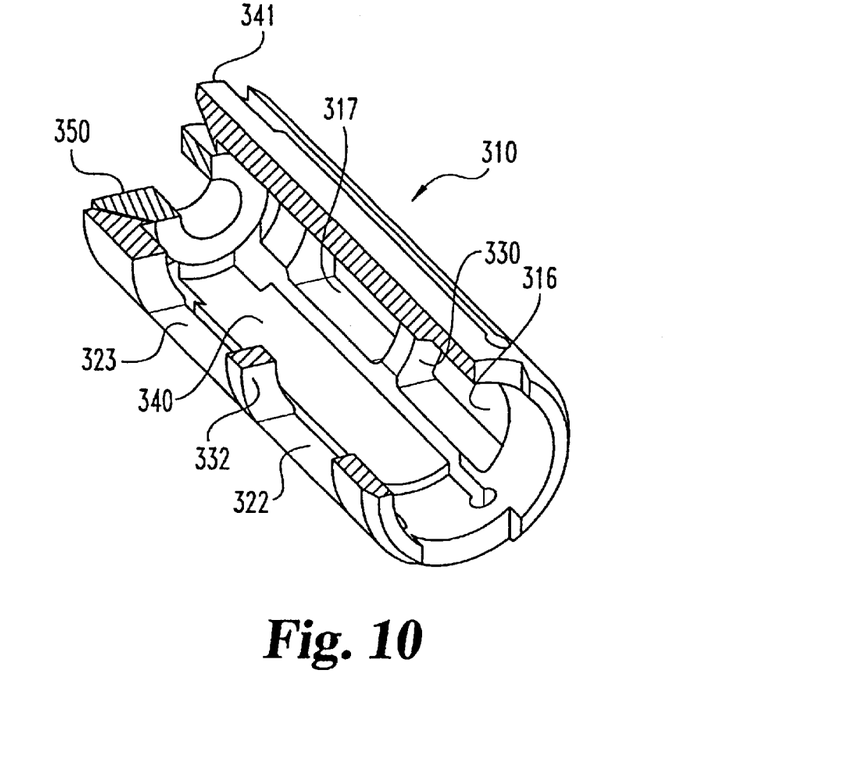
FIG. 10 is a partial cross-sectional perspective view of the expandable cage of FIG. 8 without an external thread pattern.

Referring now to FIGS. 8 through 10, there is shown an alternative embodiment of the expandable cage of the present invention. In this embodiment, expandable cage 310 has an outer surface 311 and an external thread pattern 312 (not shown in FIG. 10). As with the embodiment of FIG. 1, expandable cage 310 includes two opposed expandable branches 324 and 324, and two opposed fixed branches 340 and 341 joined at fixed end 320. Each of these branches define inclined surfaces and interior shoulders adjacent expandable end 318 adapted to engage and receive expansion wedge 350. In contrast to the embodiment of FIG. 1, expandable branch 324 includes two bone in-growth windows 316 and 317, separated by rib 330. In a similar manner, expandable branch 326 includes two bone in-growth windows 322 and 323 separated by rib 332. The use of a plurality of bone in-growth windows in the expandable branches increases the overall strength of the branch which may be necessary for longer cages or cages constructed of relatively weak materials. While this embodiment has been shown with two windows per each expandable branch, it is contemplated that more than two bone in-growth windows may be utilized without deviating from the spirit and scope of the invention.

Figure 6:
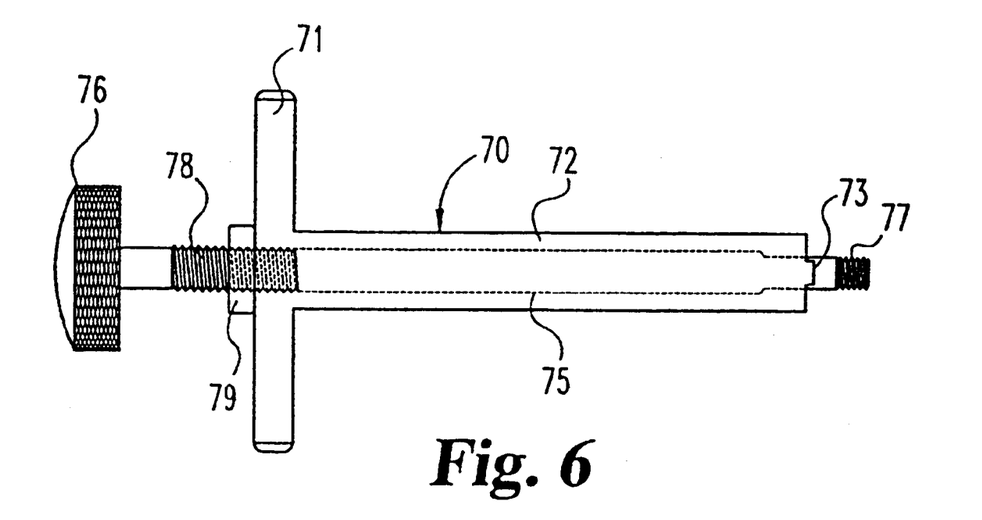
FIG. 6 is an elevational view of an insertion tool according to one embodiment of the present invention.

Referring now to FIG. 6, there is shown an insertion tool 70 suitable for use with an expandable cage according to the present invention. Insertion tool 70 includes an outer sleeve 72 having a driving projection 73 adapted to engage driving groove 46 of expandable cage 10. While insertion tool 70 is illustrated with only projection 73, it will be understood that the device includes an opposing projection (not shown) for mating with a driving groove (not shown) disposed opposite driving groove 46 on cage 10. Insertion tool 70 further includes handle 71 adapted to transmit rotational force to outer sleeve 72 to rotationally insert cage 10. Outer sleeve 72 includes an internal chamber, which is occupied by insertion tool inner shaft 75. On the distal end 77, insertion tool inner shaft 75 includes an externally threaded area adapted to engage the correspondingly internally threaded central opening 56 of expansion member 50. At the proximal end of inner shaft 75 there is a handle 76 for providing rotational force to inner shaft 75. A series of external threads 78 are formed on inner shaft 75 adjacent handle 76. A internally threaded nut 79 is disposed about inner shaft 75 and is adapted to engage threads 78 to move inner shaft 75 with respect to outer sleeve 72.

Figure 7A:
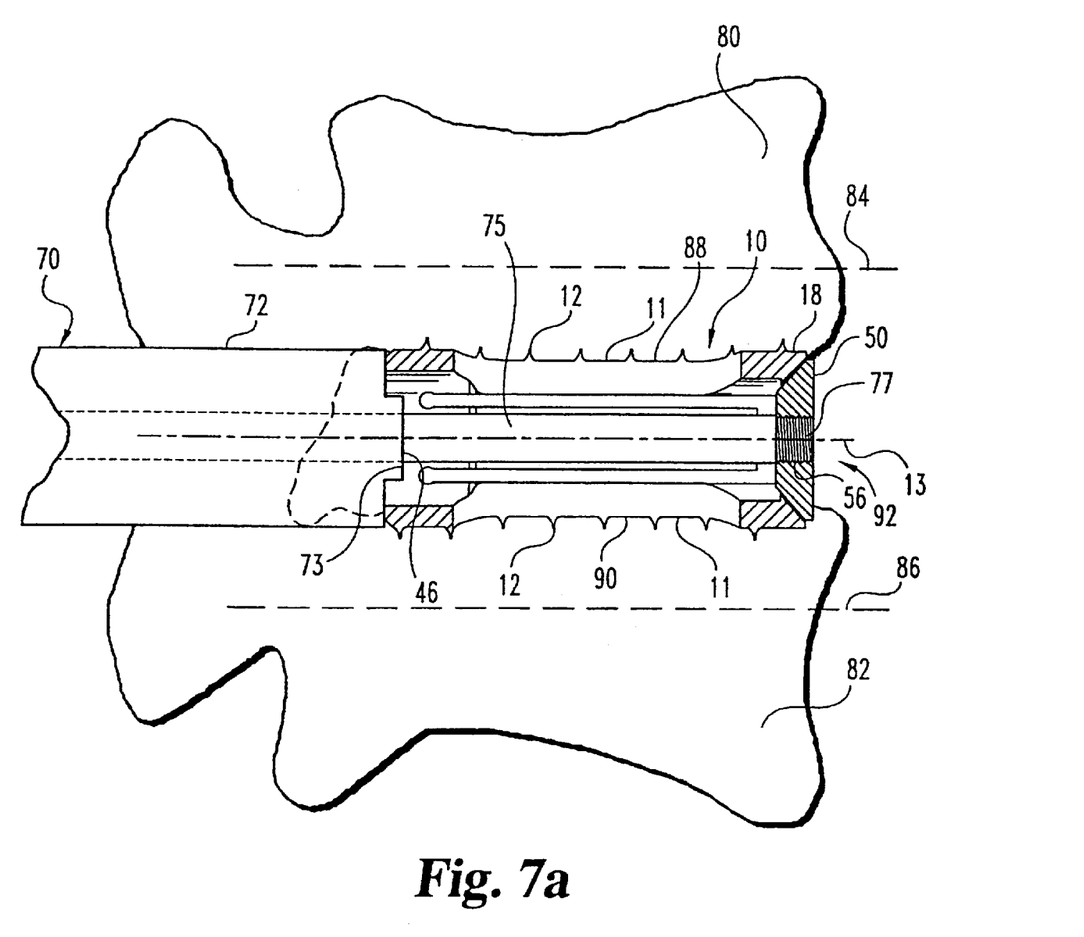
FIG. 7a is a sagittal plane view showing a partial cross-sectional side view of the expandable cage of FIG. 2b inserted between two adjacent vertebrae in an insertion configuration according to one embodiment of the present invention.

In operation, insertion tool 70 is engaged with expandable cage 10 such as shown in FIG. 7a. Driving projection 73 of outer tube 72 engages driving groove 46 of expandable cage 10 and threaded distal end 77 of inner shaft 75 threadedly engages threaded opening 56 of expansion wedge 50. In this manner, expansion wedge 50 is securely held in position adjacent the expansion end 18 while the threaded cylindrical cage is inserted into the intervertebral space. In a preferred embodiment, this device is utilized from a posterior approach to the spine with the expansion wedge 50 being positioned at the leading end of the device.

Referring to FIG. 7a, expandable cage 10 is threaded into intervertebral space 92 with thread pattern 12 engaging vertebra 80 and 82 to advance the cage into the disc space and securely hold it in position once it has reached a final position as shown in FIG. 7a. Since the expandable cage is preferably a cylinder having a uniform diameter, it may be inserted through an insertion tube having a diameter substantially equal to the thread diameter of the cage 10. As shown in FIG. 7a, the surface 88 of vertebrae 80 is in contact with outer surface 11 of cage 10. It will be understood that in many applications, a portion of the vertebral end plate will have been removed prior to cage insertion such that cage 10 engages the cancellous bone of the vertebrae. In a similar manner, the surface 90 of vertebrae 82 is in contact with the outer surface 11 of cage 10. In its initial insertion position, the alignment 84 of vertebrae 80 and the alignment 86 of vertebrae 82 are in substantial parallel alignment with longitudinal axis 13 and expandable branches 24 and 26 of cage 10.

Figure 7B:
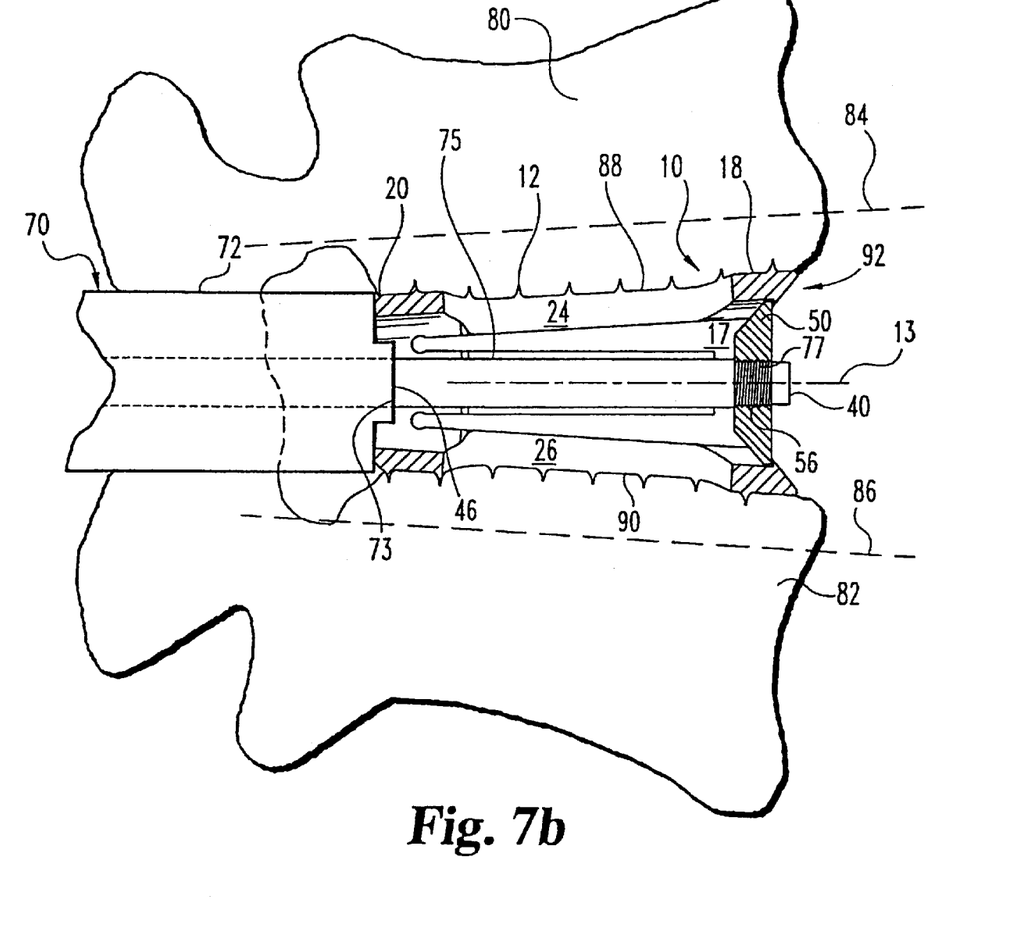
FIG. 7b is the cage of FIG. 7a shown in an expanded position according to one embodiment of the present invention.

Referring now to FIG. 7b, with threaded end 77 of the insertion device firmly engaged in threaded opening 56 of expansion wedge 50 and driving projection 73 engaged in driving groove 46, internally threaded nut 79 is rotated about external thread 78 to draw shaft 75 within outer tube 72 (FIG. 6), thereby advancing expansion wedge 50 toward fixed end 20. As expansion wedge 50 is advanced toward fixed end 20, the inclined surfaces of expansion wedge 50 force expandable branches 24 and 26 apart adjacent expandable end 18. In a similar manner, vertebra 80 and 82 are forced apart adjacent expandable end 18 such that the alignment 84 and 86 remain substantially parallel to the expandable branches 24 and 26, respectively, and not with longitudinal axis 13 of cage 10. In this manner, the lordotic curve of the spine may be established and maintained during the healing process. Moreover, the engagement of expansion wedge 50 with the previously described shoulders of each of the branches prevents the expansion wedge from being expelled from cage 10. The insertion tool may be removed and the substantially unobstructed area within interior chamber 17 may be filled with bone in-growth material to encourage bone growth through the device. Such bone in-growth material may include autograft, allograft, bone morphogenic proteins in a carrier, or other known bone growth promoting materials. Insertion and expansion of the alternative embodiment shown in FIGS. 8 through 10 is accomplished in substantially the same manner.

Figure 11:
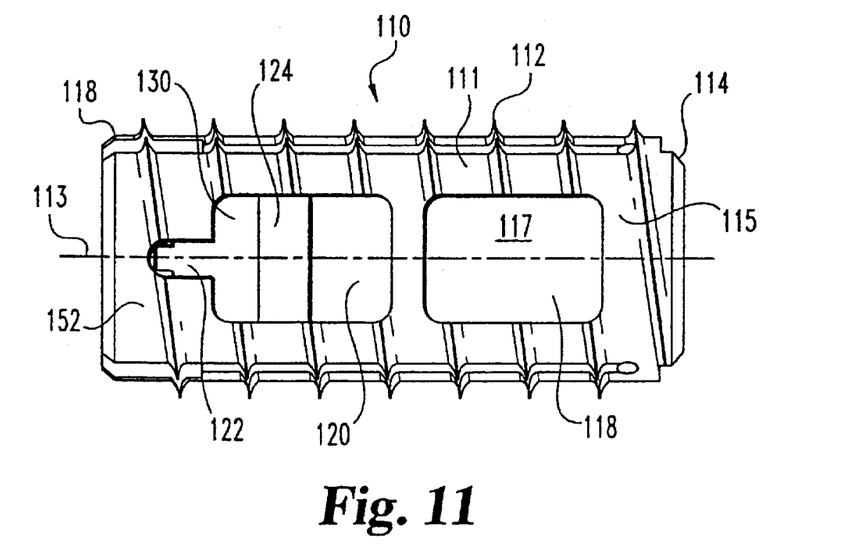
FIG. 11 is a top view of a further embodiment of an expandable cage according to the present invention.
Figure 12:
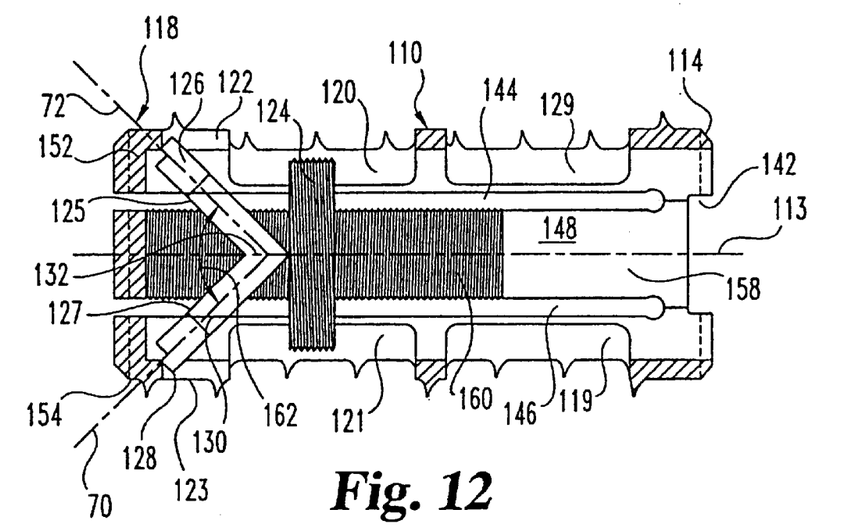
FIG. 12 is a side partial cross-sectional view of the expandable cage of FIG. 11.
Figure 13:
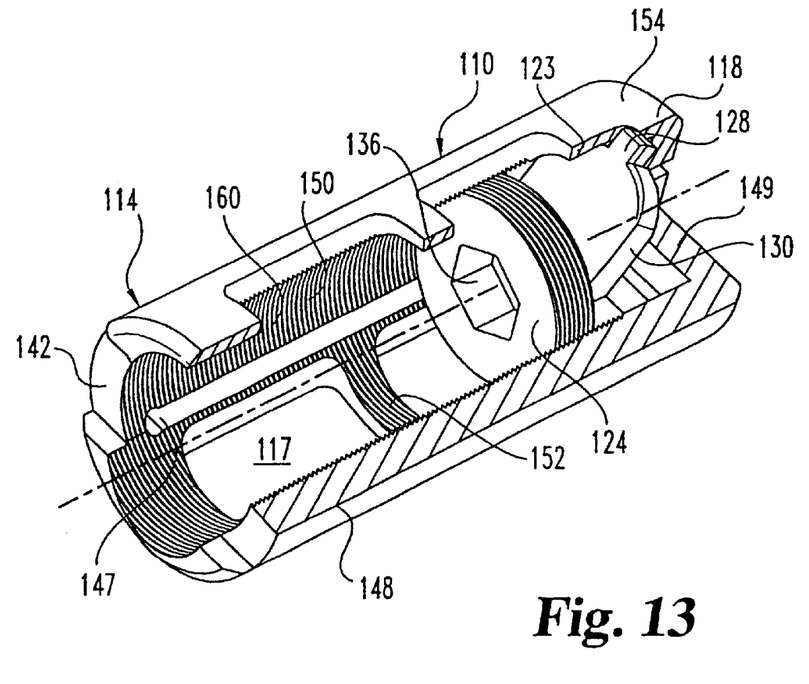
FIG. 13 is a partial cross-sectional perspective view of the expandable cage of FIG. 11, without an external thread pattern.

Referring now to FIGS. 11 through 13, there is shown a further embodiment of an expandable cage according to the present invention. As with the above-described embodiments of the invention, cage 110 is a substantially cylindrical device having an outer surface 111 defining an external thread pattern 112. Cage 110 defines a substantially cylindrical internal chamber 117. Cage 110 includes a pair of opposing expandable branches 152 and 154 separated by a pair of opposing fixed branches 148 and 150. Fixed branch 148 is separated from expandable branches 152 and 154 by channels 144 and 146, respectively. Fixed branch 150 is separated from expandable branches 154 and 152 by channel 147 and a similar channel (not shown), respectively. Cage 110 further includes bone in-growth windows 129 and 120 formed through expandable branch 152, and an identical pair of bone in-growth windows 119 and 121 formed through expandable branch 154. Each of the bone in-growth windows extend from outer surface 111 to internal chamber 117. As with the above-described embodiments, cage 110 includes a large unobstructed internal chamber 117 extending along the longitudinal axis 113 from adjacent the expandable end 118 toward the fixed end 114. In the embodiment shown in FIGS. 11 through 13, windows 120 and 121 each include a notch 122 and 123 adjacent expandable end 118, respectively.

Expander 130 is sized to be received within internal chamber 117. Expander 130 includes a first portion 125 having a projection 126 which extends into notch 122, and an opposite second portion 127 having projection 128 which extends into notch 123. Projections 126 and 128 work in conjunction with externally threaded plug 124 in maintaining the position of expander 130 within cage 110. Expander 130 further includes a bend 132. While a bend may be utilized in the preferred embodiment, it will be understood that expander 130 may include a fold or a hinge between portions 125 and 127, that allows adaptation into the reduced sized configuration shown in FIG. 12. First portion 125 includes a longitudinal axis 72 and second portion 127 includes a longitudinal axis 70. In the reduced size insertion configuration shown in FIG. 12, longitudinal axis 70 forms an angle 162 with respect to longitudinal axis 72. In a preferred embodiment, angle 162 is approximately 90°, although other angles are contemplated. In an expanded configuration (not shown), the angle between longitudinal axes 70 and 72 may approach 180°, with a 180° angle providing the maximum expansion of the device.

The internal chamber 117 is defined by the four previously described branches 148, 150, 152, and 154, each defining a portion of thread pattern 160 (only partially shown in FIG. 12). Plug 124 includes a corresponding external thread adapted to engage thread pattern 160. In a preferred embodiment, a connecting portion 149 extends between fixed branches 148 and 150 to limit splaying of the fixed branches as threaded plug 124 is advanced toward expandable end 118. Threaded plug 124 further includes a central opening 136 adapted to engage an insertion tool extension. In a preferred embodiment, central opening 136 is formed in a hexagonal pattern to accept a similar hexagonally shaped insertion tool (not shown). Cage 110 further includes a driving groove 142 adjacent fixed end 114, adapted for engagement with a driving tool projection to permit insertion of cage 110 between two adjacent bony structures. The driving tool of FIG. 6 may be utilized with cage 110 with the exception that the driving tool inner shaft 75 would include a hexagonally shaped portion at distal end 77. It will be understood that as threaded plug 124 is threadedly advanced towards expandable end 118, it urges expander 130 into an expanded condition, thereby forcing branches 152 and 154 apart. As shown in FIG. 13, the expansion mechanism of the present invention provides a large internal cavity to receive bone growth promoting material.

Figure 14:
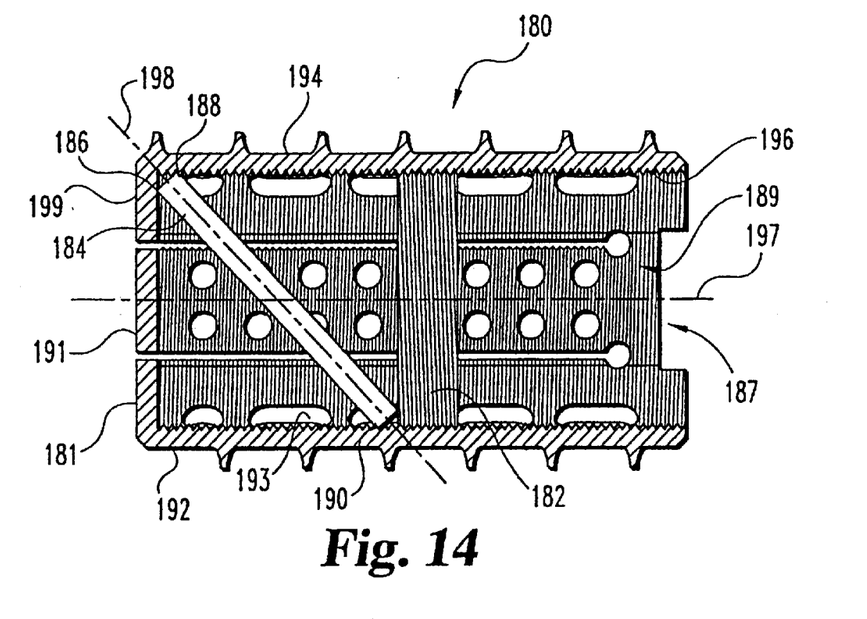
FIG. 14 is a side partial cross-sectional view of a further embodiment of the present invention.

A further embodiment according to the present invention is shown in FIG. 14. Cage 180 is fashioned in a similar manner to cage 110 with the exception that it includes a plurality of smaller bone in-growth windows rather than two large windows in expandable branches 192 and 194. Variations of the number, size, shape and location of bone in-growth windows as may be dependent on the bone in-growth characteristics desired and the material properties of the cage is contemplated by the present invention. Further, the mechanism for expansion differs in that expander 184 is a substantially planar device, i.e. no bends or hinge, having a longitudinal axis 198. Expander 184 is substantially planar and has a first end 188 engaged in corner 186 formed between expandable branch 194 and end wall 199. The opposite end 190 engages and moves along inner surface 193 of expandable branch 192. Threaded plug 182 threadedly engages internal thread pattern 196 formed along the internal surfaces of the branches. It will be understood that in the unexpanded condition, axis 198 is skewed with respect to longitudinal axis 197 of cage 180. However, as threaded plug 182 advances towards expandable end 181, expander 184 moves towards an upright position with axis 198 moving towards a perpendicular arrangement with axis 197. The movement of expander 184 towards an upright position expands cage 180. In the expanded position, there is a large unobstructed internal chamber 189 extending from plug 182 to opening 187 adjacent fixed end 195. Thus, the large internal chamber 189 may be packed with bone in-growth material to promote fusion between adjacent vertebra.

Figure 15:
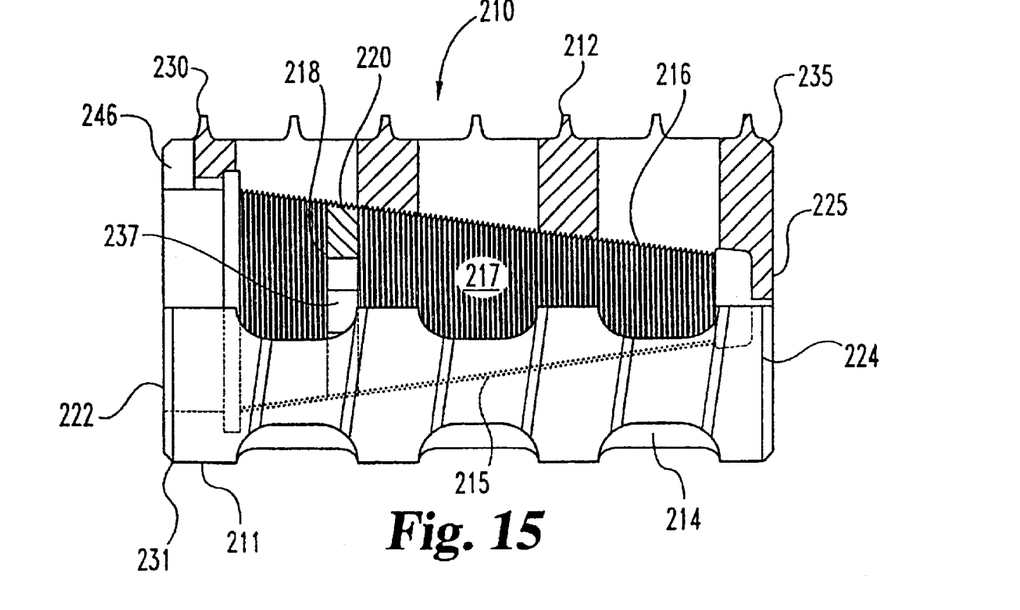
FIG. 15 is a side partial cross-sectional side view of yet a further embodiment of the present invention.

Referring now to FIG. 15, there is shown still a further embodiment of the present invention. Cage 210 includes an outer surface 211 having a thread pattern 212 defined thereon. Cage 210 includes a driving groove 246 adapted to receive a driving tool such as that previously disclosed herein. Cage 210 further includes a plurality of windows 214 communicating from exterior surface 211 to interior chamber 217. Internal chamber 217 is defined by inclined surfaces 216 and 215 (shown in dash), sloping from the expandable end 222 towards the fixed end 224. The slope of inclined surfaces 216 and 215 could also be reversed to allow expansion by movement of the plug 218 in an opposite direction. Plug member 218 includes an external thread pattern adapted to engage with thread pattern 220 of surfaces 216 and 215. It will be understood that as plug member 218 is threadedly advanced toward fixed end 224, branches 230 and 231 are spread apart from one another. As shown in FIG. 15, branch 230 includes an area of reduced width 225, adapted to deform as plug member 218 is advanced. As shown, plug member 218 includes a central opening 237 adapted to receive an insertion tool extension to provide rotational force. Further, while driving groove 246 is shown formed on expandable end 222, it will be understood that for some insertion techniques, it will be desirable to have insertion tool groove 246 formed on fixed end 224. Moreover, a central aperture may be formed through fixed end 224 for passage of an insertion tool extension for engagement with plug 218.

While plugs 124 of the embodiment of FIG. 11, plug 182 of the embodiment of FIG. 14 and plug 218 of the embodiment of FIG. 15 have been shown and described as having a series of external threads for engagement with a corresponding thread pattern defined on the branches of the device, it will be understood that all the branches, or only the fixed branches of each of the devices, may be formed to define a series of ratchets. With a ratchet configuration, each of the plugs 124, 182, and 218 may be defined as having an outer surface adapted to advance over the ratchets to expand the device while having a trailing portion adapted to engage the ratchets to prevent expulsion. In this manner, the plugs may be advanced without threading. When utilizing this technique, the insertion tool may be adapted to securely hold the outer cage to prevent its further advancement as a result of the pushing or pulling force exerted on the plug members. In addition to modifications to the plug, the cage itself may be configured for push-in insertion and can be in shapes other than cylinders.

Cages according to the present invention are preferably formed of a biocompatible material having sufficient strength to withstand the loads that will be placed upon them for a given application. Additionally, in the preferred embodiments the material should have sufficient flexibility to undergo at least a small amount of deformation as a result of the expansion process. Alternatively, for some devices, it may be desirable to provide hinge points rather than permit the material to undergo a deformation. Most preferably, the material utilized to form the cages of the present invention is a medical grade titanium alloy. However, the devices could be formed of stainless steel, various types of plastic, various composites including carbon fiber devices, and bone or bone substitutes.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An interbody fusion apparatus, comprising:
 a hollow body having an outer bone engaging surface and an inner surface defining an internal chamber and a retaining mechanism, said body having a fixed portion and an expandable portion and defining at least a first branch and a second branch, said first branch and said second branch interconnected at said fixed portion, and said first branch moveable with respect to said second branch at said expandable portion;

an expansion member sized to be at least partially received within said internal chamber and having an outer surface adapted to engage said retaining mechanism, whereby movement of said expansion member within said internal chamber urges said first branch to move with respect to said second branch thereby expanding said expandable portion, said expansion member retained in position by engagement with said retaining mechanism of the body; and an insertion tool having an outer sleeve adapted to engage said body to transmit compressive force and an inner shaft moveably disposed within said outer sleeve and sized to be inserted into at least a portion of said interior chamber, said inner shaft having a proximal end and a distal end, said distal end configured to removably engage said expansion member, whereby movement of said inner shaft with respect to said outer sleeve moves said expansion member in relation to said body.

2. The apparatus of claim 1, wherein said expansion member includes a central opening having a thread pattern and said distal end of said inner shaft includes a corresponding external thread pattern.

3. The apparatus of claim 1, wherein said expansion member includes a central hexagonal opening and said distal end of said inner shaft includes a corresponding external hexagonal shape.

4. The apparatus of claim 1, wherein said body further defines a driving groove and said outer sleeve defines a corresponding mating driving projection.

5. A method for insertion of an expandable interbody fusion device between a pair of vertebral bodies, comprising:

providing an expandable fusion cage having an external bone engaging surface, at least two branches, each of the branches having a fixed portion and at least one of the branches having a movable portion, the at least two branches forming an internal chamber defining a retaining mechanism, and an expansion member sized to be at least partially received within the internal chamber and configured for engagement with the retaining mechanism and the movable portion;

inserting the expandable cage between two adjacent vertebrae;

positioning the movable portion adjacent a vertebra;

moving the expansion member within the internal chamber and against the moveable portion to expand the cage with the movable portion of the at least one branch expanding at a greater rate than another of the at least two branches; and engaging the expansion member with the retaining mechanism to limit movement of the expansion member.

6. The method of claim 5, further including packing the internal chamber with material to promote bone in-growth.

7. An expandable fusion cage adapted to be inserted between a pair of vertebral bodies, comprising:

a body having an outer bone engaging surface and an inner surface defining an internal chamber and a retaining mechanism, said body defining at least a first branch, said branch having a fixed portion connected to said body and an expandable portion movable with respect to said body, said body defining at least a second branch connected to said body; and an expansion mechanism sized to be at least partially received within said internal chamber and to engage said expandable portion, said expansion mechanism having an outer surface adapted to engage said retaining mechanism, whereby movement of said expansion mechanism within said internal chamber urges said first branch expandable portion to move with respect to said body thereby expanding said body, said expansion mechanism moving said first branch expandable portion at a greater rate than said second branch, said expansion mechanism retained in position by engagement with said retaining mechanism of the body.

8. The expandable fusion cage of claim 7, wherein said bone engaging surface is an external thread.

9. The expandable fusion cage of claim 7, wherein said retaining mechanism is a thread pattern defined on said inner surface and said expansion mechanism includes an externally threaded plug configured for engagement with said thread pattern.

10. The expandable fusion cage of claim 7, wherein said retaining mechanism is an internal shoulder and said expansion mechanism is a wedge adapted to engage said shoulder.

11. The expandable fusion cage of claim 7, wherein said body defines a third branch opposing said first branch, said third branch having a fixed portion connected to said body and an expandable portion, whereby movement of said expansion mechanism within said internal chamber urges both said first and third branches apart.

12. An expandable cage adapted to be inserted between a pair of vertebral bodies, comprising:

a tubular body having an outer bone engaging surface and an inner surface defining an interior chamber and a retaining mechanism, said body includes a fixed end and an expandable end and further including four longitudinal channels extending between said outer surface and said inner surface and from said expandable end toward said fixed end, said channels defining an opposing first and second branches separated by opposing third and fourth branches; and an expansion mechanism having an outer surface configured to engage said inner surface and said retaining portion, whereby said expansion mechanism is moved against said inner surface to move said expandable end to expand said body, said expansion mechanism expanding said opposing first and second branches at a substantially greater rate than said opposing third and fourth branches, and said expansion mechanism retained in position by engagement with said retaining mechanism.

13. The expandable cage of claim 13, wherein said retaining mechanism includes at least one flange defined adjacent said inner surface and said expansion member includes a shoulder cooperable with said flange to maintain the position of said expansion member.

14. The expandable cage of claim 12, wherein said retaining mechanism is a thread pattern and said expansion member includes a corresponding external thread pattern.

15. The expandable cage of claim 12, wherein said bone engaging surface is an external thread.

16. The expandable cage of claim 12, wherein said body further defines bone in-growth openings between said inner surface and said outer surface.

17. The expandable cage of claim 12, wherein said interior chamber comprises at least 50% of the volume of the device, thereby allowing a substantial amount of bone growth promoting matter to be inserted into the interior chamber.

18. The expandable cage of claim 12, wherein said expansion member defines a central opening providing communication with said interior chamber.

19. An expandable fusion cage adapted to be inserted between a pair of vertebral bodies, comprising:
- a body having an outer bone engaging surface and an inner surface defining an internal chamber, said body defining at least two branches, each of said at least two branches having a fixed portion and at least one of the branches having a movable portion; and
- an expansion mechanism at least partially disposed within said internal chamber whereby movement of said expansion mechanism along said internal chamber causes said body to expand with said at least one branch expanding at a greater rate than another of said at least two branches.

20. The expandable fusion cage of claim 19, wherein said body includes a retaining mechanism adapted to engage said expansion mechanism to retain said expansion mechanism in position relative to said body.

21. The expandable of claim 19, wherein said body further defines bone in-growth openings between said inner surface and said outer surface.

22. The device of claim 19, wherein said interior chamber comprises at least 50% of the volume of the device, thereby allowing a substantial amount of bone growth promoting matter to be inserted into the interior chamber.

* * * * *

UNITED STATES PATENT AND TRADEMARK OFFICE
CERTIFICATE OF CORRECTION

PATENT NO. : 6,436,140 B1
DATED : August 20, 2002
INVENTOR(S) : Mingyan Liu et al.

It is certified that error appears in the above-identified patent and that said Letters Patent is hereby corrected as shown below:

Column 12,
Line 50, please change "claim 13" to -- claim 12 --.

Column 14,
Line 7, please insert -- fusion cage -- between "expandable" and "of claim".
Line 10, please change "device" to -- expandable fusion cage --.

Signed and Sealed this

Fourth Day of February, 2003

JAMES E. ROGAN
*Director of the United States Patent and Trademark Office*